United States Patent [19]
Sanchez De Leon-Rodriguez Roda

[11] Patent Number: 6,129,927
[45] Date of Patent: Oct. 10, 2000

[54] PLANT CARE PRODUCT APPLICABLE BY SPRAY METHODS AND PROCESS FOR THE MANUFACTURE OF SAID PRODUCT

[75] Inventor: Juan Antonio Sanchez De Leon-Rodriguez Roda, Valencia, Spain

[73] Assignee: Food Machinery Espanola, S.A., Valencia, Spain

[21] Appl. No.: 09/162,519

[22] Filed: Sep. 29, 1998

[30] Foreign Application Priority Data

Sep. 29, 1997 [ES] Spain ..................... 9702031

[51] Int. Cl.$^7$ ................... A01N 43/50; A01N 43/64; A01N 43/76
[52] U.S. Cl. ............................................. 424/405
[58] Field of Search ............................................. 424/405

[56] References Cited

U.S. PATENT DOCUMENTS

| | | | |
|---|---|---|---|
| 3,630,697 | 12/1971 | Dulling et al. | 431/288 |
| 3,954,868 | 5/1976 | Von Schmeling et al. | 260/570 R |
| 5,013,746 | 5/1991 | Van Gestel et al. | 514/365 |
| 5,456,745 | 10/1995 | Roveger et al. | 106/128 |
| 5,851,952 | 12/1998 | Karp et al. | 504/251 |

OTHER PUBLICATIONS

Tsumura–Hasegawa et al., *BIOSIS*, 92:29831, 1992.
Habeebunnisa, *Chemical Abstracts*, 78:157957, 1973.
Wright et al., *Chemical Abstracts*, 102:108049, 1986.
Szegoe et al., *Chemical Abstracts*, 100:134292, 1985.

*Primary Examiner*—Mukund J. Shah
*Assistant Examiner*—B. Jayaram
*Attorney, Agent, or Firm*—Flynn, Thiel, Boutell & Tanis, P.C.

[57] ABSTRACT

This product, which can be applied by spray methods, contains fungicides, preservatives (antioxidants), sprouting control products (applicable to warehoused potatoes) and agricultural insecticides (post-harvest).

The fungicides contain Imazalil, Methyl-thiophanate; Ortho-phenylphenol; Alkali-earth silicates and a combustible wax.

The preservatives contain Diphenylamine, Ethoxyquin, Alkali-earth silicates and a combustible wax.

The sprouting control products contain Chlorpropham, silicates and a combustible wax.

The insecticides contain Propoxur, Pyretrines, silicates and a combustible wax.

The process for manufacturing the products involves the following operations: mixing the ingredients; grinding; homogenization; and packaging of the product in a metal spray can with an air chamber.

This invention can be used for the treatment of units to be used for storing fruits and vegetables which are either empty or containing said fruits and vegetables.

9 Claims, 1 Drawing Sheet

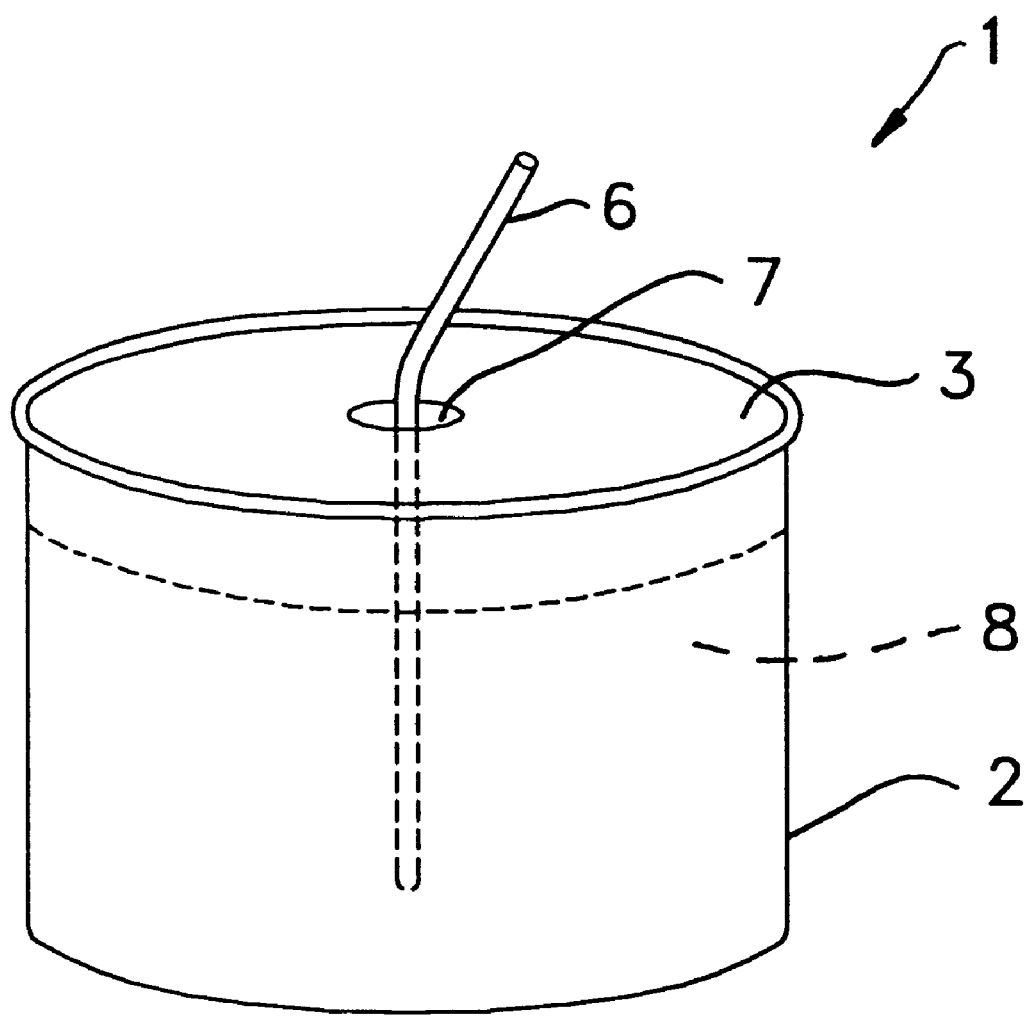

PLANT CARE PRODUCT APPLICABLE BY SPRAY METHODS AND PROCESS FOR THE MANUFACTURE OF SAID PRODUCT

OBJECT

The object of the present invention which is to be protected under this patent consists of a sprayable plant care product and the process for manufacturing said product, which is specially suitable for treating fruits and vegetables after harvesting.

As a result of the above, the effect thereof is preferably applicable both for the treatment of empty units used for the storage and handling of fruits and vegetables (cold storage or degreening chambers, warehouses, trucks or railcars, etc.) and for spraying directly on the fruit and vegetable products.

BACKGROUND INFORMATION

The application of insecticide products dispersed in the form of fumes and used for the disinsecting of closed, empty units is already known.

This application is usually made by means of smoke pots which, as a result of involving a known method, is easy and convenient to use.

The contents of these pots include:

a) An inert matrix comprised of a porous product which is not involved in the combustion (i.e., a silicate).

b) An active ingredient which is borne and dispersed by the gases produced in the combustion, forming a dry smoke.

c) A combustible product capable of continuing to burn once ignited, such as a combustion wax, which is a hydrocarbon compound which can be combusted in the presence of oxygen.

d) An air chamber at the top for supplying the oxygen necessary for the combustion.

The fuel is initially ignited by means of a fuse which is inserted inside the fuel and which is lit once the unit has been cleared and closed.

The gas by-products of the combustion build up pressure inside the pot, from which they spurt out through a hole in the center of the top, carrying along the active material which is dispersed in the smoke and expands with it, permeating the entire area.

BRIEF DESCRIPTION OF THE DRAWING

The FIGURE shows a spray pot which can be used in the present invention. The spray pot 1 comprises a cylindrical body 2, a cover or lid 3 provided on the cylindrical body 2 and a wick 6 extending into the interior of the cylindrical body 2 through an aperture 7 provided in the lid 3. A combustible composition 8 according to the present invention is contained within the body 2 of the spray pot and, when ignited, exits the spray pot 1 via the aperture 7.

DESCRIPTION OF THE INVENTION

The biocidal process described above has not been used to date in plant care application on fruits and vegetables.

The FIGURE illustrates a spray pot configuration which can be used in the present invention.

To bring this process into being, lengthy research focused mainly on the effect of the active ingredient on the different applications advocated has been required for the full-scale development thereof.

Independently of the research conducted for selecting the most effective products, it has been necessary to set out a distinction between those to be used preferably for disinfecting the environment and those used selectively for directly treating the fruits and vegetables.

In fact, one and the other are subject to differing requirements, said requirements revolving around gauging the amount of build-up left on the fruits or vegetable treated in order to ensure that they are within the limits of tolerance set forth in each consumer country.

Apart from the above, it has been necessary to determine the optimum concentrations of active ingredient given in the form of percentages of the net weight of the pot contents such that they will also fulfill the objectives of plant care effectiveness and economy of use without overdoses or underdoses.

All of the research required for achieving the desired, anticipated results having been completed, ideal products have been selected to comprise the active ingredient, taken exclusively from among those authorized by the Ministry of Agriculture for plant care treatments in variable proportions although with preferred percentages.

Taking into account all of the aforementioned criteria, the compositions of these spray products are as follows:

a) Fungicide: (Formula 1)

| PRODUCT | FIELD OF APPLICATION | PREFERRED % |
| --- | --- | --- |
| Imazalil | 0%–50% | 10% |
| Methyl-thiophanate | 0%–50% | 12% |
| Ortho-phenylphenol | 0%–50% | 25% |
| Alkali-earth silicates | 5%–75% | 40% |
| Combustible wax | 5%–50% | 13% | b) Fungicide: (Formula 2)

| PRODUCT | FIELD OF APPLICATION | PREFERRED % |
| --- | --- | --- |
| Thiabendazole, Procloraz, Fosetyl-Al, Guazatine, Dicloran, Yprodione, Procymidone | 0%–50% | 25% |
| Alkali-earth silicates | 5%–75% | 50% |
| Combustible wax | 5%–50% | 25% | c) Preservatives (Antioxidants)

| PRODUCT | FIELD OF APPLICATION | PREFERRED % |
| --- | --- | --- |
| Diphenylamine, Ethoxyquin | 0%–50% | 25% |
| Alkali-earth silicates | 5%–75% | 50% |
| Combustible wax | 5%–50% | 25% | d) sprouting Control Products: (for spraying warehoused potatoes)

| PRODUCT | FIELD OF APPLICATION | PREFERRED % |
| --- | --- | --- |
| Chlorpropham | 0%–50% | 25% |
| Alkali-earth silicates | 5%–75% | 50% |
| Combustible wax | 5%–50% | 25% | e) Agricultural Insecticides: (Post-harvest)

| PRODUCT | FIELD OF APPLICATION | PREFERRED % |
|---|---|---|
| Propoxur, Pyretrines | 0%–50% | 25% |
| Alkali-earth silicates | 5%–75% | 50% |
| Combustible wax | 5%–50% | 25% |

The process for manufacturing the different products entails, in any case, the following operations:

Mixing of both the active and inactive ingredients.

Grinding of the mixture into fine particles.

Homogenization of the ground mixture.

Packaging of the product in the metal spray pot with air chamber.

The treatment described of the fruits and vegetables affords the following advantages:

Fast, direct and widespread action without further handling.

As a result of the above, economical application.

Possibility for use as back-up treatment in those cases in which changes in the healthiness of the fruits or vegetables are detected or the anticipated storage time is extended.

Dry treatment, entailing the advantage over bathing of not adding any moisture which can add pollution.

What is claimed is:

1. A plant care product which is applied by combustion of the product and contains a fungicide, said fungicide comprising a first composition containing up to 50% enilconazole, up to 50% o-phenylphosphate, 5 to 75% of an alkali earth metal silicate and 5 to 50% of a combustible wax or a second composition containing at least one member selected from the group consisting of thiabendazole, prochloraz, fosetyl-al, guazatine, dicloran, yprodione and procymidone in a total amount of up to 50%, 5 to 75% of an alkali earth metal silicate and 5 to 50% of a combustible wax, said percentages being based on percent by weight.

2. The plant care product of claim 1, wherein said first composition comprises 10% enilconazole, 25% o-phenylphosphate, 40% of the alkali metal silicate and 13% of the combustion wax and said second composition comprises 25% of the at least one member, 50% of the alkali earth metal silicate and 25% of the combustion wax.

3. A plant care product which is applied by combustion of the product and contains a preservative, said preservative comprising up to 50% in total of at least one member selected from the group consisting of diphenylamine and ethoxyquin, from 5 to 75% of an alkali metal silicate and 5 to 50% of a combustible wax, said percentages being based on percent by weight.

4. The plant care product of claim 3, wherein said preservative comprises 25% of the at least one member, 50% of the alkali metal silicate and 25% of the combustion wax.

5. A plant care product which is applied by combustion of the product and contains a sprouting control agent, said sprouting control agent comprising up to 50% chlorpropham, from 5 to 75% of an alkali earth metal silicate and from 5 to 50% of a combustible wax, said percentages being based on percent by weight.

6. The plant care product of claim 5, wherein said sprouting control agent comprises 25% of chlorpropham, 50% of an alkali earth metal silicate and 25% of a combustible wax.

7. A plant care product which is applied by combustion of the product and contains an insecticide, said insecticide comprising up to 50% of at least one member selected from the group consisting of propoxur and a pyretrine, from 5 to 75% of an alkali earth metal silicate and from 5 to 50% of a combustible wax, said percentages being based on percent by weight.

8. The plant care product of claim 7, wherein said insecticide comprises 25% of the at least one member, 50% of the alkali metal silicate and 25% of the combustible wax.

9. A process for preparing a plant care system for applying a plant care composition by combustion of the composition, said process comprising the steps of: mixing a plant care compound, an alkali metal silicate and a combustible wax to form a mixture; grinding the mixture into fine particles; homogenizing the ground mixture; and loading the homogenized ground mixture into a spray pot to form the plant care system.

* * * * *